(12) United States Patent
Hestad et al.

(10) Patent No.: US 8,740,945 B2
(45) Date of Patent: Jun. 3, 2014

(54) DYNAMIC STABILIZATION SYSTEM USING POLYAXIAL SCREWS

(75) Inventors: Hugh D. Hestad, Edina, MN (US); Daniel A. Carlson, St. Louis Park, MN (US); Daniel G. Brown, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 634 days.

(21) Appl. No.: 12/755,520

(22) Filed: Apr. 7, 2010

(65) Prior Publication Data

US 2011/0251644 A1    Oct. 13, 2011

(51) Int. Cl.
*A61B 17/70* (2006.01)

(52) U.S. Cl.
USPC .......................... 606/257; 606/254; 606/272

(58) Field of Classification Search
CPC ........... A61B 17/7007; A61B 17/7019; A61B 17/7037
USPC ......... 606/254–264, 265, 266, 268, 269–278, 606/319, 328, 305–308
See application file for complete search history.

(56) References Cited

U.S. PATENT DOCUMENTS

| | | |
|---|---|---|
| 4,743,260 A | 5/1988 | Burton |
| 5,176,708 A | 1/1993 | Frey et al. |
| 5,375,823 A | 12/1994 | Navas |
| 5,540,688 A | 7/1996 | Navas |
| 5,562,660 A | 10/1996 | Grob |
| 5,725,582 A | 3/1998 | Bevan et al. |
| 5,782,831 A | 7/1998 | Sherman |
| RE36,221 E | 6/1999 | Breard |
| 6,248,106 B1 | 6/2001 | Ferree |
| 6,290,700 B1 | 9/2001 | Schmotzer |
| 6,328,740 B1 | 12/2001 | Richelsoph |
| 6,610,079 B1 | 8/2003 | Li |
| 6,802,844 B2 | 10/2004 | Ferree |
| 6,986,771 B2 | 1/2006 | Paul |
| 6,989,011 B2 | 1/2006 | Paul |
| 7,008,424 B2 | 3/2006 | Teitelbaum |
| 7,029,475 B2 | 4/2006 | Panjabi |
| 7,137,985 B2 | 11/2006 | Jahng |

(Continued)

FOREIGN PATENT DOCUMENTS

| | | |
|---|---|---|
| EP | 0516567 A1 | 12/1992 |
| EP | 0669109 A1 | 8/1995 |

(Continued)

OTHER PUBLICATIONS

Davis, Reginald et al., "Dynesys LIS Less Invasive Surgery," Dynamic Stabilization System, Zimmer Spine Inc., 2005.

(Continued)

*Primary Examiner* — Jan Christopher Merene
*Assistant Examiner* — Atiya Mahmud
(74) *Attorney, Agent, or Firm* — Seager, Tufte & Wickhem, LLC

(57) ABSTRACT

A spinal stabilization system including an insert positionable in the channel of the housing of a poly-axial pedicle screw which allows for locking the housing of the poly-axial pedicle screw from pivotal movement through a clamping force generated by rotational engagement of a fastener with the housing while clamping a cord of a support construct in the housing of the poly-axial pedicle screw through direct contact of the fastener against the cord.

10 Claims, 13 Drawing Sheets

(56) References Cited

U.S. PATENT DOCUMENTS

| | | |
|---|---|---|
| 7,326,210 B2 | 2/2008 | Jahng et al. |
| 7,641,673 B2 | 1/2010 | Le Couedic et al. |
| 2002/0035366 A1 | 3/2002 | Walder et al. |
| 2003/0220643 A1 | 11/2003 | Ferree |
| 2004/0049189 A1 | 3/2004 | Le Couedic et al. |
| 2004/0215191 A1 | 10/2004 | Kitchen |
| 2004/0225289 A1 | 11/2004 | Biedermann et al. |
| 2005/0010220 A1 | 1/2005 | Casutt et al. |
| 2005/0056979 A1 | 3/2005 | Studer et al. |
| 2005/0065416 A1 | 3/2005 | Subotics |
| 2005/0085812 A1* | 4/2005 | Sherman et al. ............... 606/61 |
| 2005/0085815 A1 | 4/2005 | Harms et al. |
| 2005/0096652 A1 | 5/2005 | Burton |
| 2005/0124991 A1 | 6/2005 | Jahng |
| 2005/0143737 A1 | 6/2005 | Pafford et al. |
| 2005/0154390 A1 | 7/2005 | Biedermann et al. |
| 2005/0177157 A1 | 8/2005 | Jahng |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0277922 A1* | 12/2005 | Trieu et al. ................... 606/61 |
| 2006/0106380 A1 | 5/2006 | Colleran et al. |
| 2006/0106381 A1 | 5/2006 | Ferree et al. |
| 2006/0111715 A1 | 5/2006 | Jackson |
| 2006/0142758 A1* | 6/2006 | Petit ................................ 606/61 |
| 2006/0173454 A1 | 8/2006 | Spitler et al. |
| 2006/0195093 A1 | 8/2006 | Jahng |
| 2006/0200129 A1 | 9/2006 | Denti |
| 2006/0212033 A1 | 9/2006 | Rothman et al. |
| 2006/0229615 A1 | 10/2006 | Abdou |
| 2006/0247638 A1 | 11/2006 | Trieu et al. |
| 2007/0005062 A1 | 1/2007 | Lange et al. |
| 2007/0005063 A1 | 1/2007 | Bruneau et al. |
| 2007/0016200 A1 | 1/2007 | Jackson |
| 2007/0055244 A1* | 3/2007 | Jackson ........................ 606/61 |
| 2007/0100341 A1 | 5/2007 | Reglos et al. |
| 2007/0118119 A1 | 5/2007 | Hestad |
| 2007/0129729 A1 | 6/2007 | Petit et al. |
| 2007/0179501 A1 | 8/2007 | Firkins |
| 2007/0198088 A1 | 8/2007 | Biedermann et al. |
| 2007/0225710 A1 | 9/2007 | Jahng et al. |
| 2007/0233075 A1* | 10/2007 | Dawson ........................ 606/61 |
| 2007/0233087 A1 | 10/2007 | Schlapfer |
| 2007/0233095 A1 | 10/2007 | Schlaepfer |
| 2007/0239158 A1 | 10/2007 | Trieu et al. |
| 2007/0270821 A1 | 11/2007 | Trieu et al. |
| 2007/0270860 A1 | 11/2007 | Jackson |
| 2007/0293862 A1 | 12/2007 | Jackson |
| 2008/0009863 A1 | 1/2008 | Bond et al. |
| 2008/0021459 A1 | 1/2008 | Lim |
| 2008/0021465 A1 | 1/2008 | Shadduck et al. |
| 2008/0039843 A1 | 2/2008 | Abdou |
| 2008/0051787 A1 | 2/2008 | Remington et al. |
| 2008/0058812 A1 | 3/2008 | Zehnder |
| 2008/0091213 A1 | 4/2008 | Jackson |
| 2008/0140076 A1 | 6/2008 | Jackson |
| 2008/0140133 A1 | 6/2008 | Allard et al. |
| 2008/0147122 A1 | 6/2008 | Jackson |
| 2008/0161857 A1 | 7/2008 | Hestad et al. |
| 2008/0177317 A1 | 7/2008 | Jackson |
| 2008/0183216 A1 | 7/2008 | Jackson |
| 2008/0195153 A1* | 8/2008 | Thompson .................. 606/257 |
| 2008/0215095 A1 | 9/2008 | Biedermann et al. |
| 2008/0215100 A1* | 9/2008 | Matthis et al. ................ 606/309 |
| 2008/0234737 A1* | 9/2008 | Boschert ....................... 606/254 |
| 2008/0234738 A1 | 9/2008 | Zylber et al. |
| 2008/0234744 A1* | 9/2008 | Zylber et al. .................. 606/264 |
| 2008/0262551 A1* | 10/2008 | Rice et al. ..................... 606/268 |
| 2008/0275456 A1 | 11/2008 | Vonwiller et al. |
| 2008/0294198 A1 | 11/2008 | Jackson |
| 2008/0300633 A1 | 12/2008 | Jackson |
| 2008/0319482 A1* | 12/2008 | Jackson ........................ 606/246 |
| 2008/0319486 A1 | 12/2008 | Hestad et al. |
| 2008/0319490 A1* | 12/2008 | Jackson ........................ 606/308 |
| 2009/0005817 A1* | 1/2009 | Friedrich et al. .............. 606/246 |
| 2009/0012562 A1 | 1/2009 | Hestad et al. |
| 2009/0030464 A1 | 1/2009 | Hestad et al. |
| 2009/0036924 A1 | 2/2009 | Egli et al. |
| 2009/0082815 A1 | 3/2009 | Zylber et al. |
| 2009/0093845 A1 | 4/2009 | Hestad et al. |
| 2009/0093846 A1 | 4/2009 | Hestad |
| 2009/0099606 A1 | 4/2009 | Hestad et al. |
| 2009/0112265 A1 | 4/2009 | Hudgins et al. |
| 2009/0118767 A1 | 5/2009 | Hestad et al. |
| 2009/0177232 A1* | 7/2009 | Kiester ......................... 606/260 |
| 2009/0198281 A1 | 8/2009 | Rice et al. |
| 2009/0216281 A1 | 8/2009 | Vonwiller et al. |
| 2010/0010542 A1* | 1/2010 | Jackson ........................ 606/254 |
| 2010/0094348 A1* | 4/2010 | Biedermann et al. .......... 606/264 |
| 2010/0145394 A1* | 6/2010 | Harvey et al. ................. 606/302 |
| 2010/0331887 A1 | 12/2010 | Jackson et al. |
| 2011/0009906 A1* | 1/2011 | Hestad et al. ................. 606/278 |
| 2011/0066187 A1* | 3/2011 | Fang et al. .................... 606/254 |

FOREIGN PATENT DOCUMENTS

| | | |
|---|---|---|
| EP | 0669109 B1 | 5/1999 |
| EP | 1523949 A1 | 4/2005 |
| EP | 1719468 A1 | 11/2006 |
| EP | 1523949 B1 | 6/2007 |
| FR | 2715057 A1 | 7/1995 |
| FR | 2775583 A1 | 9/1999 |
| FR | 2844180 A1 | 3/2004 |
| FR | 2867057 A1 | 9/2005 |
| NL | 7610576 A | 3/1978 |
| WO | 9519149 A1 | 7/1995 |
| WO | 9905980 A1 | 2/1999 |
| WO | 9944527 A1 | 10/1999 |
| WO | 2004024011 A1 | 3/2004 |
| WO | 2004089244 A2 | 10/2004 |
| WO | 2005037110 A2 | 4/2005 |
| WO | 2005037150 A1 | 4/2005 |
| WO | 2005087121 A1 | 9/2005 |
| WO | 2006066685 A1 | 6/2006 |
| WO | 2007044795 A2 | 4/2007 |
| WO | 2007087476 A1 | 8/2007 |
| WO | 2008006098 A2 | 1/2008 |
| WO | 2008013892 A2 | 1/2008 |
| WO | 2008021319 A2 | 2/2008 |
| WO | 2008034130 A2 | 3/2008 |
| WO | 2008134703 A2 | 11/2008 |

OTHER PUBLICATIONS

Hestad, Hugh D. et al., "Vertebral Stabilization transition Connector," U.S. Appl. No. 12/501,793, filed Jul. 13, 2009.

Fang, Zhibin et al., "Spinal Stabilization System," U.S. Appl. No. 12/558,170, filed Sep. 11, 2009.

\* cited by examiner

DYNAMIC STABILIZATION SYSTEM USING POLYAXIAL SCREWS

TECHNICAL FIELD

The disclosure is directed to a vertebral stabilization system. More particularly, the disclosure is directed to a dynamic stabilization system including a support construct configured to be used with poly-axial pedicle screws.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. One example of a dynamic stabilization system is the Dynesys® system available from Zimmer Spine, Inc. of Minneapolis, Minn. Such dynamic stabilization systems typically include a flexible member positioned between pedicle screws installed in adjacent vertebrae of the spine. A flexible cord can be threaded through the bore in the flexible member and secured to the pedicle screws while cooperating with the flexible member to permit mobility of the spine. The pedicle screw currently used in the Dynesys® system is a mono-axial pedicle screw which may present limitations during installation of the Dynesys® system in some instances.

There is an ongoing need to provide alternative devices, assemblies, systems and/or methods that can function to alleviate pain or discomfort, provide stability, such as dynamic stability, and/or restore a range of motion to a spinal segment of a spinal column. Accordingly, it may be desirable to utilize poly-axial screws in a dynamic stabilization system, such as the Dynesys® system.

SUMMARY

The disclosure is directed to several alternative designs, materials and methods of manufacturing medical device structures and assemblies and uses thereof.

Accordingly, one illustrative embodiment is a spinal stabilization system including a polyaxial pedicle screw, an insert, a support construct and a fastener. The polyaxial pedicle screw includes a housing and a threaded shaft extending from the housing. The threaded shaft is pivotable relative to the housing to a plurality of angular positions. The housing includes a channel extending from a first side of the housing to a second side of the housing. The insert is positionable in the channel of the housing. The insert includes an open channel extending from a first end of the insert to a second end of the insert. The support construct includes a spacer and a cord extendable through a lumen of the spacer. The cord is positionable in the open channel of the insert such that a first portion of the cord extends from the first side of the housing of the polyaxial pedicle screw and a second portion of the cord extends from the second side of the housing of the polyaxial pedicle screw. The fastener is configured to rotatably engage the housing of the pedicle screw, wherein rotational engagement of the fastener with the housing causes the fastener to directly contact the cord to exert a clamping force directly on the cord.

Another illustrative embodiment is a spinal stabilization system including a polyaxial pedicle screw, a spool, a spacer, a flexible cord, and a fastener. The polyaxial pedicle screw includes a housing pivotably coupled to a threaded shaft. The housing includes a channel extending from a first side of the housing to a second side of the housing. The spool includes a first flange, a second flange and a medial portion extending between the first flange and the second flange. The spool is configured to engage the housing of the pedicle screw such that the medial portion is positioned in the channel with the first flange positioned adjacent the first side of the housing and the second flange positioned adjacent the second side of the housing. The spacer has a first end, a second end and a lumen extending through the spacer from the first end to the second end. The first end of the spacer is positionable in abutting contact with the first flange of the spool. The flexible cord is configured to extend through the lumen of the spacer and through the spool such that a first portion of the flexible cord extends from the first flange of the spool and a second portion of the flexible cord extends from the second flange of the spool. The fastener is configured to rotatably engage the housing of the pedicle screw to directly contact and press against the cord such that the cord is compressed between the fastener and a surface of the spool.

In yet another illustrative embodiment is a method of stabilizing a spinal segment. The method includes securing a polyaxial pedicle screw to a vertebra. The polyaxial pedicle screw includes a housing pivotably coupled to a threaded shaft. The housing includes a channel extending from a first side of the housing to a second side of the housing. An insert is inserted into the channel of the housing of the polyaxial pedicle screw. The insert includes an open channel extending from a first end of the insert to a second end of the insert. A flexible cord is positioned in the open channel of the insert such that a first portion of the flexible cord extends from the first end of the insert and a second portion of the flexible cord extends from the second end of the insert. A fastener is rotatably engaged with the housing a first rotational amount such that the fastener directly contacts and presses against the cord to exert a compressive force on the cord.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
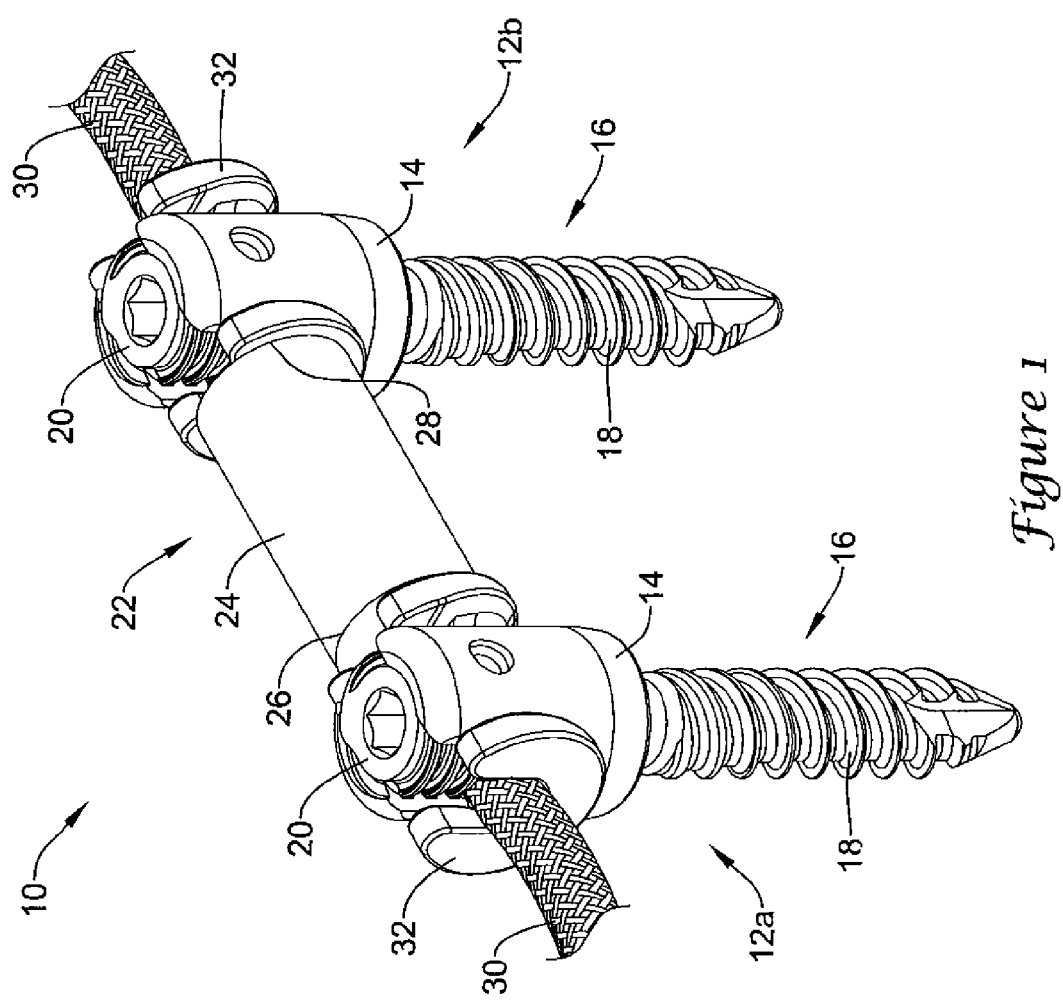
FIG. 1 is a perspective view of an exemplary spinal stabilization system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a spinal fixation system 10 for stabilizing a portion of a spinal column, such as one or more spinal segments of a spinal column. As used herein, a spinal segment is intended to refer to two or more vertebrae, the intervertebral disc(s) between the vertebrae and other anatomical elements between the vertebrae. For example, a spinal segment may include first and second adjacent vertebrae and the intervertebral disc located between the first and second vertebrae. The spinal stabilization system 10 may provide dynamic stabilization to a spinal segment, preserving and/or allowing for a range of motion of the spinal segment.

In some embodiments, the spinal stabilization system 10 may be used to treat discogenic low back pain, degenerative spinal stenosis, disc herniations, facet syndrome, posterior element instability, adjacent level syndrome associated with spinal fusion, and/or other maladies associated with the spinal column.

The spinal stabilization system 10 may include one or more or a plurality of vertebral anchors, depicted as pedicle screws 12. However, in some embodiments the vertebral anchors may be vertebral hooks (e.g., laminar hooks) or other types of fastening members for attachment to a bony structure such as a vertebra of the spinal column. Each of the pedicle screws 12 may be configured to be secured to a vertebra of a spinal column. For instance, the first pedicle screw 12a may be secured to a first vertebra and the second pedicle screw 12b may be secured to a second vertebra. Additional pedicle screws 12 may be present in instances in which the spinal stabilization system 10 spans three or more vertebra of the spinal column.

Figure 3:
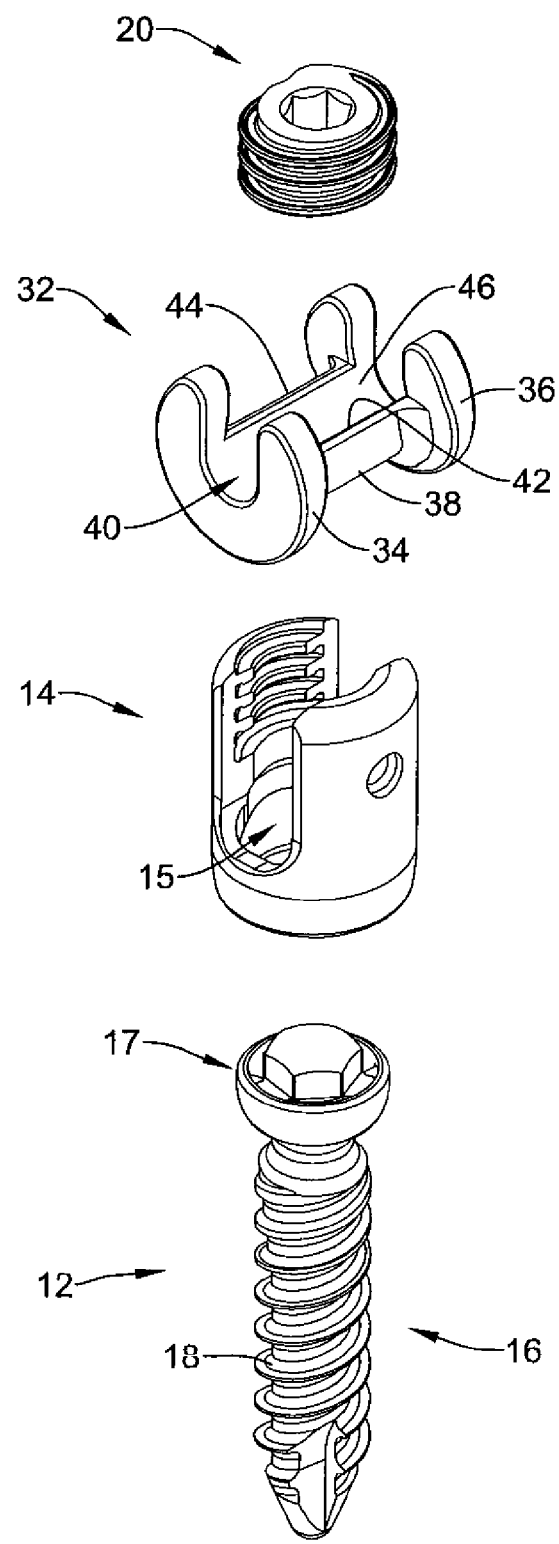
FIG. 3 is an exploded view of the pedicle screw assembly of FIG. 2.

The pedicle screw 12 may include a housing 14 and a shaft 16, which may include threads 18, extending from the housing 14. The housing 14 may include a channel, such as a U-shaped channel extending from one side of the housing 14 to an opposite second side of the housing 14. The channel 15 may be defined between opposing legs of the housing 14. The shaft 16 may be configured to be installed into a bony region of a vertebra of the spinal column. For example, the shaft 16 may be installed into a pedicle of a vertebra, or other region of a vertebra. The shaft 16 may extend along a longitudinal axis. The pedicle screw 12 depicted in the Figures is a poly-axial pedicle screw which allows the housing 14 to be pivotable relative to the shaft 16 to a plurality of angular positions relative to the longitudinal axis. The pedicle screw 12, as shown in FIG. 3, may include a head portion 17 at the end of the shaft 16 which is received in the housing 14. The housing 14 may be pivotable relative to the head portion 17 of the shaft 16.

The pedicle screw 12 may include a securing element, such as a threaded fastener 20 (e.g., a set screw, cap) configured to rotatably engage the housing 14 to secure a portion of a support construct 22 to the pedicle screw 12. For example, the threaded fastener 20 may include threads which mate with threads formed in the housing 14. In other embodiments, the fastener 20 may include one or more flanges, cam surfaces, or other engagement features that engage with one or more channels, grooves, surfaces, or other engagement features of the housing 14 through rotation of the fastener 20. The fastener 20 may be rotatably engaged between spaced apart legs of the housing 14 which define the channel 15 of the housing 14 therebetween.

The spinal stabilization system 10 may also include one or more, or a plurality of support constructs 22 extending between pedicle screws 12 of the spinal stabilization system 10. As an illustrative example, the spinal stabilization system 10 shown in FIG. 1 includes a support construct 22 extending between the first pedicle screw 12a and the second pedicle screw 12b.

The support construct 22 may be constructed of a plurality of components in some instances. For instance, the support construct 22 may include a spacer 24, and a flexible member such as a flexible cord 30 extending through the spacer 24, as well as other components if desired.

In some embodiments, the spacer 24 may be an annular spacer having a lumen (not shown) extending from a first end 26 to a second end 28 of the spacer 24. For example, in some embodiments the spacer 24 may be a cylindrical member having a lumen extending therethrough. In other embodiments, the spacer 24 may be molded, extruded, or otherwise formed over and/or around the cord 30. The spacer 24 may be positioned between the housing 14 of the first pedicle screw 12a and the housing 14 of the second pedicle screw 12b. In some embodiments, the spacer 24 may be formed from polycarbonate urethane (PCU), although it will be recognized that various other materials suitable for implantation within the human body and for providing stabilization of the spine while maintaining flexibility may be used. In other embodiments, the spacer 24 can be constructed of other materials such as metal, polymeric materials, or combinations of materials.

The cord 30 may extend from the housing 14 of the first pedicle screw 12a to the housing 14 of the second pedicle screw 12b. In one embodiment, the cord 30 may be formed from polyethylene-terephthalate (PET), although it will be recognized that various other materials suitable for implantation within the human body and for providing stabilization of the spine while maintaining flexibility may be used. In other embodiments, the cord 30 can be constructed of other flexible materials such as metal, polymeric materials, or combinations of flexible materials. It is noted that during a medical procedure the portions of the cord 30 which are shown extending from the channels of the pedicle screws 12a, 12b may be trimmed as desired to reduce and/or eliminate the portion of the cord 30 extending from the pedicle screws 12a, 12b.

When implanted in a patient, the cord 30 of the spinal stabilization system 10 may limit the range of flexion of the spinal segment, whereas the spacer 24 may limit the range of extension of the spinal segment. For instance, the cord 30 may be placed in tension and the spacer 24 may be placed in compression between the pedicle screws 12a, 12b.

Figure 4:
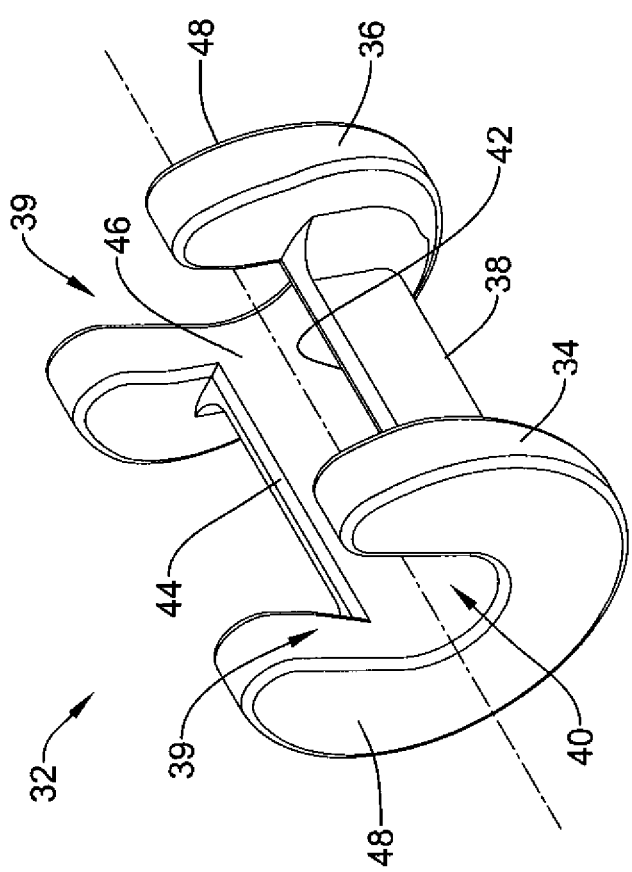
FIG. 4 is a perspective view of the insert of the pedicle screw assembly of FIG. 2.

The spinal stabilization system 10 may also include inserts 32 configured to be inserted into the channels of the housing 14 of the pedicle screws 12. One possible embodiment of the insert 32 is further illustrated in FIG. 4. The inserts 32, which may be considered spools in some instances, may include a first flange 34 proximate a first end of the insert 32, a second flange 36 proximate the second end of the insert 32, and a medial portion 38 intermediate the first flange 34 and the second flange 36 and extending therebetween. The insert 32 may have end surfaces 48 configured to abut an end surface of the spacer 24. For instance, when assembled an end surface 48 of an insert 32 coupled with the first pedicle screw 12a may abut an end surface of the spacer 24 proximate the first end 26 of the spacer 24 and an end surface 48 of an insert 32 coupled with the second pedicle screw 12b may abut an end surface of the spacer 24 proximate the second end 28 of the spacer 24.

Figure 2:
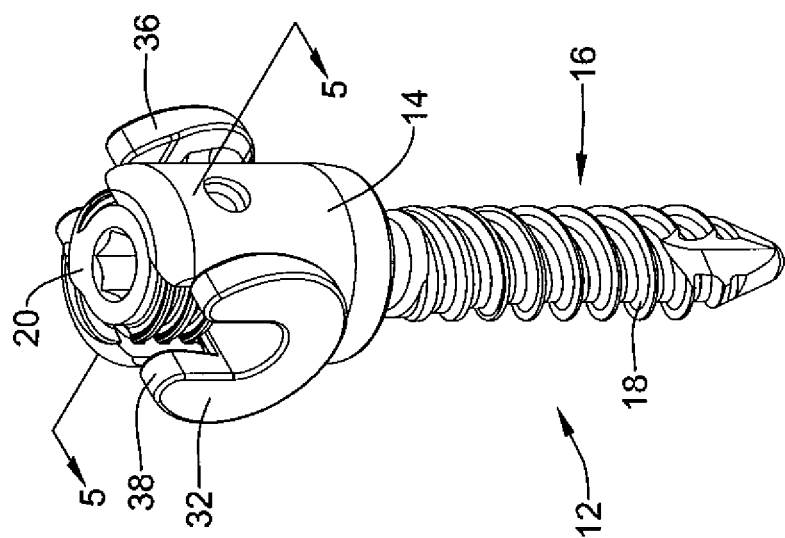
FIG. 2 is a perspective view of a pedicle screw assembly of the spinal stabilization system of FIG. 1, including an insert positioned in a the channel of the housing of the pedicle screw.

As shown in FIG. 2, the insert 32 may be configured such that the medial portion 38 is positionable in the channel 15 (shown in FIG. 3) of the housing 14 of the pedicle screw 12 with the first flange 34 positioned exterior of the housing 14 and facing the first side of the housing 14 and the second flange 36 positioned exterior of the housing 14 and facing the second side of the housing 14. The insert 32 may be positioned in the channel 15 in a top-loaded fashion in which the insert 32 is moved into the channel 15 of the housing 14 in a direction generally perpendicular to the longitudinal axis of the channel 15 of the housing 14.

The insert 32 may include an open channel 40 extending from the first end of the insert 32 to the second end of the insert 32 along a longitudinal axis parallel to the longitudinal axis of the channel 15 through the housing 14. As used herein the term "open channel" is intended to refer to a conduit which is not enclosed by a peripheral surface extending entirely around a periphery of the conduit. In other words, the open channel 40 may be open to the exterior of the insert 32 along at least a portion of its length in addition to being open at its ends such that the open channel 40 is open laterally from the longitudinal axis of the open channel 40. In some instances, the open channel 40 may otherwise be referred to as a furrow, recess or depression extending from the first end of the insert 32 to the second end of the insert 32.

The open channel 40 may be configured to receive the cord 30 therein. For instance, the open channel 40 allows the cord 30 to be inserted into the open channel 40 of the insert 32 in a direction generally perpendicular to the longitudinal axis of the open channel 40. Each of the first flange 34 and the second flange 36 may include a slot 39 extending from a periphery of the flange 34, 36 to the open channel 40 to allow the cord 30 to be inserted into the open channel 40 while extending outward from the first and second flanges 34, 36.

The open channel 40 may be defined as a recessed area of the insert 32 between a first edge 42 and a second edge 44 of the insert 32. The first and second edges 42, 44 may be upper edges or extents of the open channel 40 and/or the medial portion 38 of the insert 32. In some instances, the first and second edges 42, 44 may extend generally parallel to the longitudinal axis of the open channel 40. In some embodiments, the open channel 40 may include a surface 46, such as a concave surface, extending between the first and second edges 42, 44 for receipt of the cord 30 thereagainst. When implanted, the cord 30 may be compressed between the fastener 20 and the surface 46 of the insert 32.

Figure 4A:
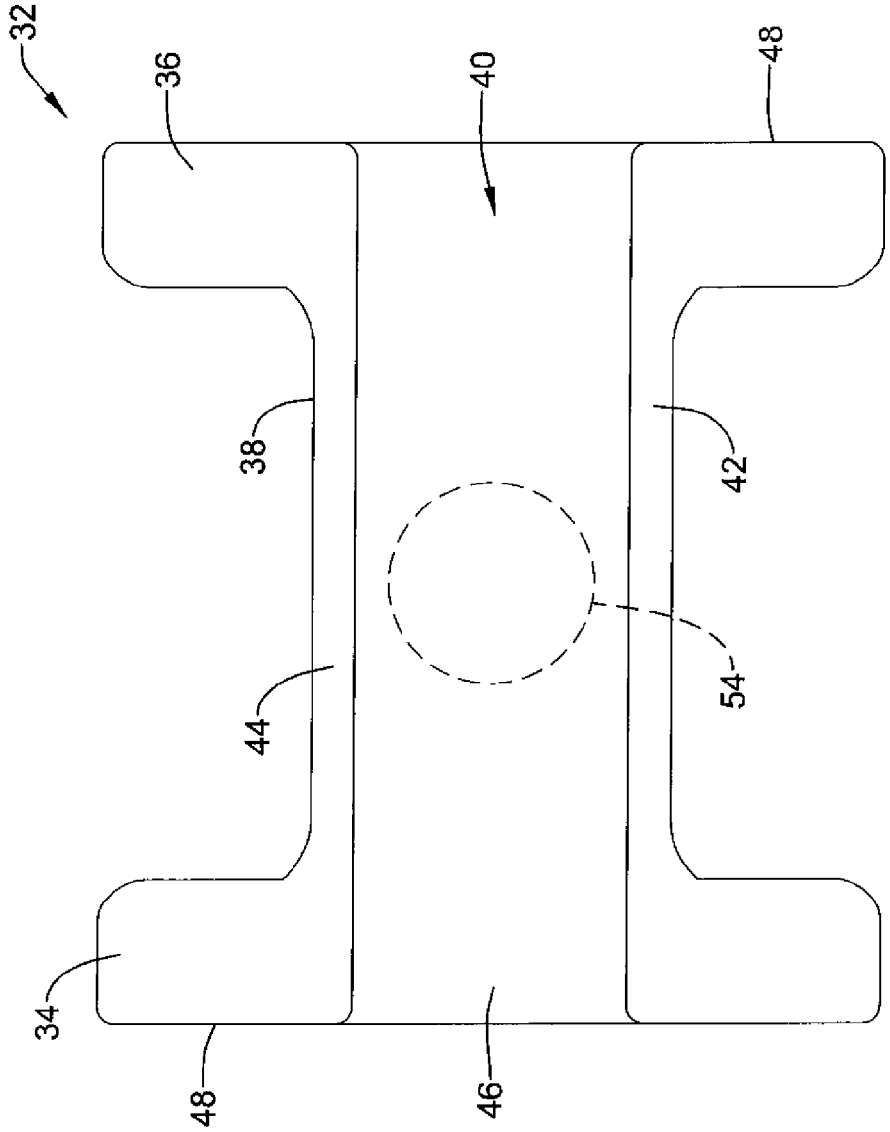
FIG. 4A is a top view of the insert shown in FIG. 4.
Figure 4B:
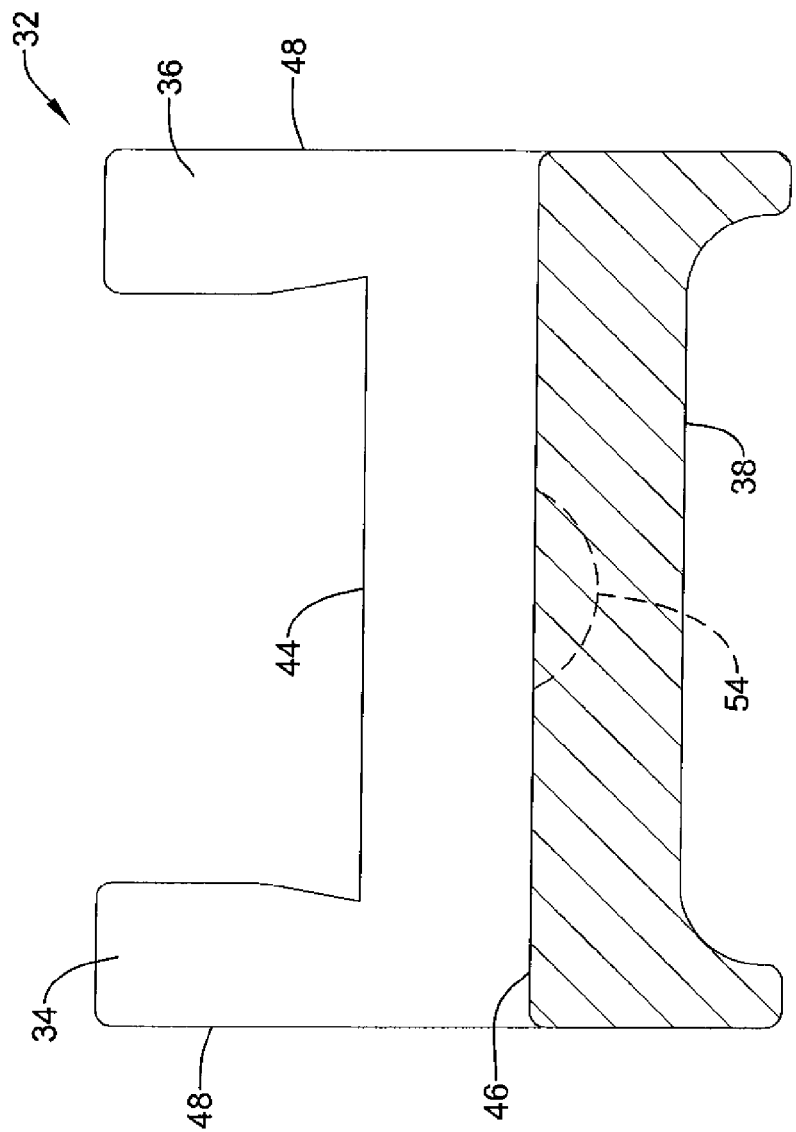
FIG. 4B is a longitudinal cross-sectional view of the insert shown in FIG. 4.

In some instances, the surface 46 may include any mechanical gripping means such as, but not limited to, one or more threads, ribs, projecting grooves, teeth, posts, spikes, and/or serrations or combination thereof. The mechanical gripping means may increase the purchase of the cord 30 between the fastener 20 and the insert 32 as will be further described herein. Additionally or alternatively, the insert 32 may include a depression 54 extending into the insert 32 from the base of the concave surface 46 of the open channel 40. One exemplary depression 54 is shown in dashed lines in FIGS. 4A and 4B as a spherically concave depression which may be axially aligned with the axis of rotation of the fastener 20 when the insert 32 is positioned in the channel 15 of the housing 14.

The presence of the depression 54 may advantageously enhance the securement of the cord 30 between the fastener 20 and the insert 32. For instance, when the cord 30 is compressed by the fastener 20, a portion of the cord 30 may be pressed into the depression 54, providing a more tortuous pathway for the cord 30 passing through the open channel 40, as shown herein at FIG. 5B. Although the depression 54 is shown with regard to the configuration of FIGS. 5A and 5B, in some instances the depression 54 may not be present.

Figure 6A:
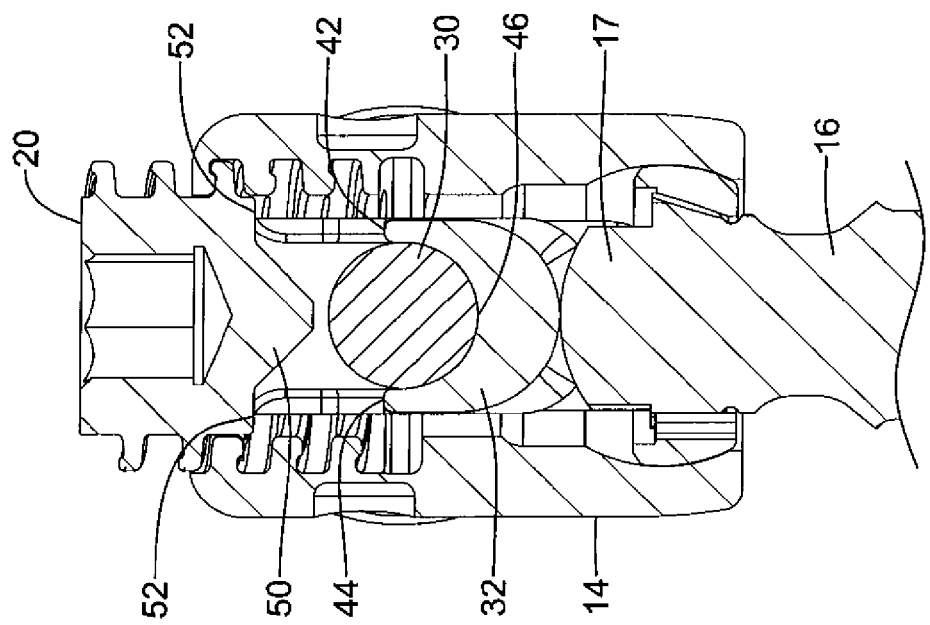
FIGS. 6A and 6B illustrate another exemplary configuration for locking the housing of a poly-axial pedicle screw from pivotal movement while clamping a cord to the pedicle screw.
Figure 6B:
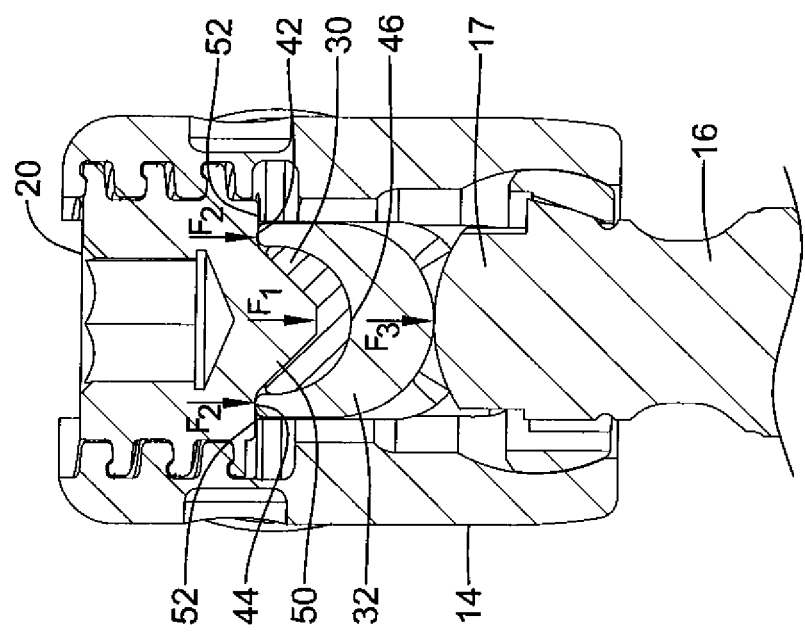

Furthermore, the depression 54, while not illustrated regarding the configuration of FIGS. 6A and 6B, may be included in such a configuration, if desired.

The presence of the insert 32 in the channel 15 of the housing 14 may facilitate locking the housing 14 from poly-axial movement relative to the shaft 16 of the pedicle screw 12 when the spinal stabilization system 10 is installed. For instance a locking force exerted by the fastener 20 may be transmitted through the insert 32 to the head portion 17 of the shaft 16 to lock the housing 14 from pivotable movement relative to the head portion 17 of the shaft 16. The insert 32, which is more rigid than the cord 30, is in direct contact with the head portion 17 of the shaft 16 to transfer the locking force exerted by the fastener 20 to the head portion 17.

Figure 5A:
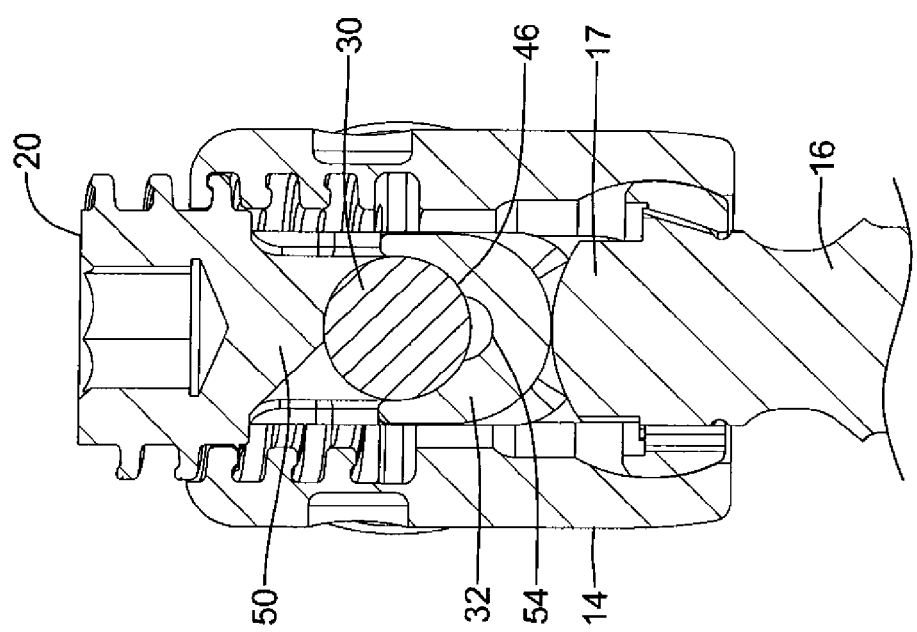
FIGS. 5A and 5B illustrate one exemplary configuration for locking the housing of a poly-axial pedicle screw from pivotal movement while clamping a cord to the pedicle screw.
Figure 5B:
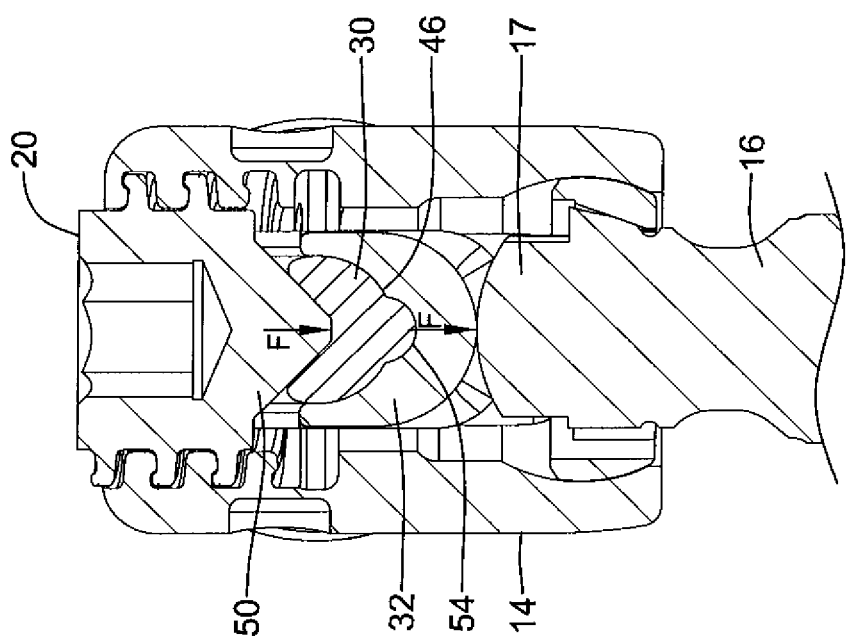

One exemplary configuration for locking the housing 14 of the poly-axial pedicle screw 12 from pivotal movement while clamping the cord 30 to the pedicle screw 12 is shown in FIGS. 5A and 5B.

As shown in FIG. 5A, the insert 32 may be inserted into the channel 15 of the housing 14 in a direction generally perpendicular to the longitudinal axis of the open channel 40. The cord 30 may also be inserted into the channel 15 of the housing 14 and into the open channel 40 of the insert 32 such that the cord 30 rests against the recessed surface 46 of the insert 32. Thus, the medial portion 38 of the insert 32 may be positioned between the head portion 17 of the shaft 16 of the pedicle screw 12 and the cord 30.

The fastener 20 may then be engaged with the housing 14, such as through rotational movement of the fastener 20 relative to the housing 14. In some instances, the fastener 20 may include a threaded portion which threadably engages a threaded portion of the housing 14, such as internally threaded portions of opposing legs of the housing 14 defining the channel 15. Rotational movement of the fastener 20 moves the fastener 20 into engagement with the cord 30. As shown in FIG. 5A, the fastener 20 may include a projection 50, such as a conical or frusta-conical tip, configured to press against and/or penetrate into the cord 30.

As shown in FIG. 5B, rotational engagement of the fastener 20 with the housing 14 causes the fastener 20 to directly contact the cord 30 to exert a clamping force F directly on the cord 30 to compress the cord 30 between the fastener 20 and the insert 32. The amount of rotation of the fastener 20, and thus axial movement of the fastener 20 along its axis of rotation, controls the magnitude of the clamping force F exerted on the cord 30 (i.e., the greater the amount of rotation of the fastener 20 results in a greater clamping force F). Deformation of the cord 30 and/or penetration into the cord 30 by the projection 50 may prevent the cord 30 from moving axially from the housing 14. Furthermore, as shown in FIG. 5B, if a depression 54 is present in the base of the open channel 40 of the insert 32, the compression of the cord 30 by the fastener 20 may displace a portion of the cord 30 into the depression 54, creating a more tortuous pathway for the cord 30 along the open channel 40. The clamping force F exerted onto the cord 30 is also transferred through the cord 30 to the insert 32 and through the insert 32 to the head portion 17 of the shaft 16 of the pedicle screw 12.

When the clamping force F is sufficiently large, the clamping force F exerted onto the head portion 17 by the insert 32 locks the housing 14 from pivotal movement relative to the head portion 17. The rigid interface between the insert 32 and the head portion 17 of the shaft 16 enhances the locking effect of the housing 14 over a configuration in which the cord 30 directly exerts a force against the head portion 17. Thus, the clamping force F generated through rotational engagement of the fastener 20 with the housing 14 both clamps the cord 30 to the insert 32 (and thus secures the cord 30 to the pedicle screw 12) and locks the housing 14 from pivotal movement relative to the shaft 16 of the pedicle screw 12.

Another exemplary configuration for locking the housing 14 of the poly-axial pedicle screw 12 from pivotal movement while clamping the cord 30 to the pedicle screw 12 is shown in FIGS. 6A and 6B.

As shown in FIG. 6A, the insert 32 may be inserted into the channel 15 of the housing 14 in a direction generally perpendicular to the longitudinal axis of the open channel 40. The cord 30 may also be inserted into the channel 15 of the housing 14 and into the open channel 40 of the insert 32 such that the cord 30 rests against the recessed surface 46 of the insert 32. Thus, the medial portion 38 of the insert 32 may be positioned between the head portion 17 of the shaft 16 of the pedicle screw 12 and the cord 30.

The fastener 20 may then be engaged with the housing 14, such as through rotational movement of the fastener 20 relative to the housing 14. In some instances, the fastener 20 may include a threaded portion which threadably engages a threaded portion of the housing 14. Rotational movement of the fastener 20 moves the fastener 20 into engagement with the cord 30. As shown in FIG. 6A, the fastener 20 may include a projection 50, such as a conical or frusta-conical tip, configured to press against and/or penetrate into the cord 30. The fastener 20 may also include a rim 52 configured to come into contact with the upper edges 42, 44 of the insert 32.

As shown in FIG. 6B, rotational engagement of the fastener 20 with the housing 14 a first rotational amount causes the fastener 20 to directly contact the cord 30 to exert a clamping force F1 directly on the cord 30 to compress the cord 30 between the fastener 20 and the insert 32. The amount of rotation of the fastener 20 up to a threshold amount, and thus axial movement of the fastener 20 along its axis of rotation up to a threshold amount, controls the magnitude of the clamping force F1 exerted on the cord 30 (i.e., the greater the amount of rotation of the fastener 20 up to a threshold amount results in a greater clamping force F1). Deformation of the cord 30 and/or penetration into the cord 30 by the projection 50 may prevent the cord 30 from moving axially from the housing 14. The clamping force F1 exerted onto the cord 30 is also transferred through the cord 30 to the insert 32 and through the insert 32 to the head portion 17 of the shaft 16 of the pedicle screw 12. Until the rim 52 of the fastener 20 contacts the edges 42, 44 of the insert 32, the locking force F3 exerted by the insert 32 onto the head portion 17 of the shaft 16 is approximately equal to the clamping force F1 exerted onto the cord 30 by the fastener 20.

The fastener 20 may be rotatably engaged with the housing 14 a first rotational amount such that the rim 52 of the fastener 20 comes into contact with the edges 42, 44 of the medial portion 38 of the insert 32. Further rotation of the fastener 20 beyond this first rotational amount does not appreciably increase the compressive force F1 exerted on the cord 30 as the distance between the fastener 20 and the surface 46 of the insert 32 does not change once the rim 52 comes into contact with the edges 42, 44. Thus, when the rim 52 of the fastener 20 contacts the edges 42, 44 of the insert 32 the clamping force F1 reaches its maximum threshold amount. The assembly may be sized and configured such that the cord 30 may be compressed between the fastener 20 and the surface 46 of the insert 32 a predetermined amount such that the threshold amount of the clamping force F1 is sufficient to clamp the cord 30 to the insert 32, and thus secure the cord 30 to the pedicle screw 12 while not letting the cord 30 move longitudinally through the open channel 40 of the insert 32.

Until the rim 52 of the fastener 20 contacts the edges 42, 44, the locking force F3 exerted onto the head portion 17 of the shaft 16 may be approximately equal to the clamping force F1 exerted directly on the cord 30 by the fastener 20. Once the rim 52 of the fastener 20 contacts the edges 42, 44, further rotational engagement of the fastener 20 a second rotational amount exerts an additional clamping force F2 directly on the edges 42, 44 of the insert 32, without further increasing the compression of the cord 30 beyond the predetermined amount. Thus, further rotation of the fastener 20 beyond the threshold amount, further increases the locking force F3 exerted on the head portion 17 of the shaft 16 of the pedicle screw 12. The locking force F3 generated beyond this threshold amount of rotational engagement between the fastener 20 and the housing 14 is approximately equal to the clamping force F1 exerted on the cord 30 from the fastener 20 plus the clamping force F2 exerted on the insert 32 from the fastener 20.

When the locking force F3 is sufficiently large, the locking force F3 exerted onto the head portion 17 by the insert 32 locks the housing 14 from pivotal movement relative to the head portion 17. The rigid interface between the insert 32 and the head portion 17 of the shaft 16 enhances the locking effect of the housing 14 over a configuration in which the cord 30 directly exerts a force against the head portion 17. Thus, the clamping forces F1, F2 generated through rotational engagement of the fastener 20 with the housing 14 both clamps the cord 30 to the insert 32 (and thus secures the cord 30 to the pedicle screw 12) and locks the housing 14 from pivotal movement relative to the shaft 16 of the pedicle screw 12.

Thus, the insert 32 of the disclosed spinal stabilization system 10 allows for locking the housing 14 of a poly-axial pedicle screw 12 from pivotal movement while clamping the cord 30 in the housing 14 of the poly-axial pedicle screw 12 through direct contact of the fastener 20 against the cord 30. The rigid interface between the insert 32 and the head portion 17 of the shaft 16 enhances the locking effect of the housing 14 over a configuration in which the cord 30 directly exerts a force against the head portion 17 of the shaft 16 of the pedicle screw 12.

Figure 7A:
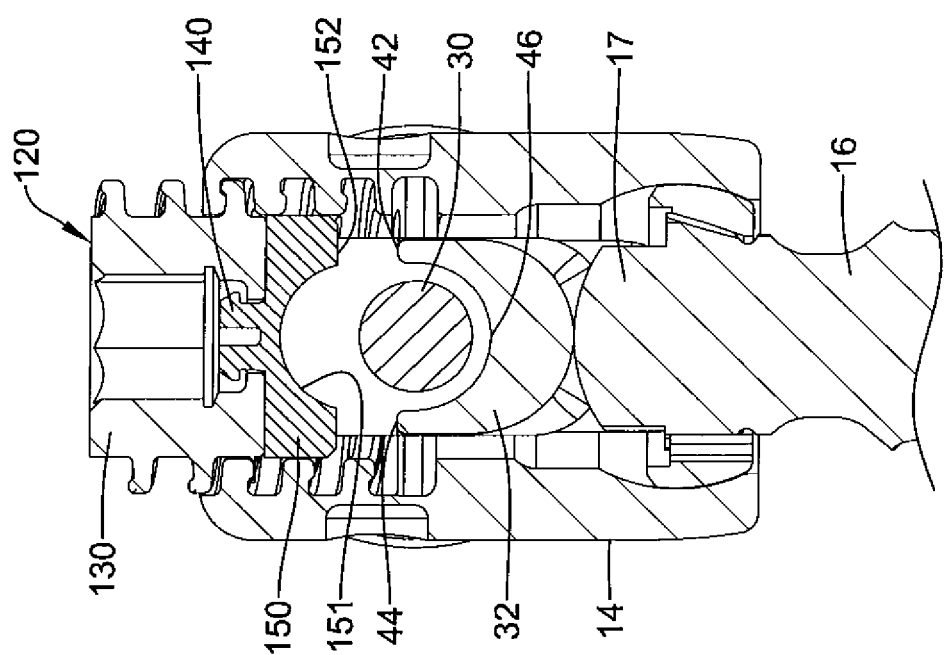
FIGS. 7A and 7B illustrate an exemplary configuration for locking the housing of a poly-axial pedicle screw from pivotal movement while capturing a cord in the housing of the pedicle screw.
Figure 7B:
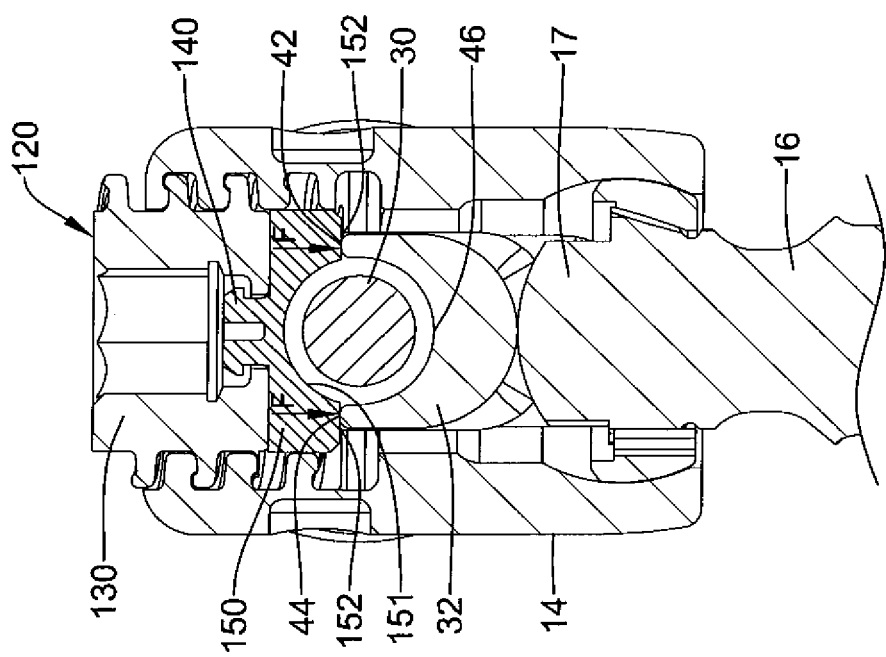

FIGS. 7A and 7B illustrate an exemplary configuration for locking the housing 14 of the poly-axial pedicle screw 12 from pivotal movement while capturing the cord 30 in the channel 15 of the housing 14 of the pedicle screw 12. In this configuration, the cord 30, while captured in the housing 14, is permitted to move longitudinally relative to the housing 14 and insert 32 since a clamping force is not applied to the cord 30.

As shown in FIG. 7A, the insert 32 may be inserted into the channel 15 of the housing 14 in a direction generally perpendicular to the longitudinal axis of the open channel 40. The cord 30 may also be inserted into the channel 15 of the housing 14 and into the open channel 40 of the insert 32 such that the cord 30 rests against the recessed surface 46 of the insert 32. Thus, the medial portion 38 of the insert 32 may be positioned between the head portion 17 of the shaft 16 of the pedicle screw 12 and the cord 30.

A fastener 120 may then be engaged with the housing 14, to capture the cord 30 in the channel 15 of the housing 14 without applying a clamping force onto the cord 30. For instance, the fastener 120 may include a first, upper component 130 rotatably coupled to a second, lower component 150. For example, the fastener 120 may include an upper threaded screw portion rotatably coupled to a lower, saddle portion. The threaded screw portion (upper component 130) may be rotated relative to the saddle portion (lower component 150) about an axis of rotation. The threaded screw portion may threadedly engage with a threaded portion of the housing 14 through rotational movement of the threaded screw portion relative to the housing 14 while the saddle portion remains in a stationary orientation relative to the housing 14. In other instances, the upper component 130 of the fastener 120 may include other engagement features, such as one or more flanges, cam surfaces, etc., for rotatably engaging an engagement portion of the housing 14. Rotational movement of the upper component 130 of the fastener 120 moves the fastener 120 into engagement with the insert 32 while capturing the cord 30 between the lower component 150 of the fastener 120 and the surface 46 of the insert 32.

The lower component 150 may be rotatably attached to the upper component 130 with a boss 140 that extends into an opening in the upper component 130. The lower component 150 of the fastener 120 may include a lower edge 152 configured to come into contact with the upper edges 42, 44 of the insert 32, while a concave cavity 151 formed in the lower edge 152 receives the cord 30 therein. The concave cavity 151, in combination with the open channel 40 of the insert 32, together form a through bore through the construct, allowing the cord 30 to freely move in an axial direction relative to the housing 14 of the pedicle screw 12.

As shown in FIG. 7B, rotational engagement of the upper component 130 of the fastener 120 with the housing 14 causes the lower edge 152 of the lower component 150 of the fastener 120 to come into contact with the edges 42, 44 of the medial portion 38 of the insert 32, thereby exerting a locking force F on the insert 32. The assembly may be sized and configured such that the cord 30 is not compressed between the fastener 20 and the surface 46 of the insert 32 when a clamping force F is exerted onto the insert 32 by the fastener 20, and thus allowing the cord 30 to move longitudinally through the bore collectively defined by the concave cavity 151 and the open channel 40 of the insert 32. Further rotation of the upper component 130 of the fastener 120 further increases the locking force F exerted on the head portion 17 of the shaft 16 of the pedicle screw 12 without applying a compressive force to the cord 30. When the locking force F is sufficiently large, the locking force F exerted onto the head portion 17 by the insert 32 locks the housing 14 from pivotal movement relative to the head portion 17. Thus, the clamping force F generated through rotational engagement of the upper component 130 of the fastener 20 with the housing 14 locks the housing 14 from pivotal movement relative to the shaft 16 of the pedicle screw 12 while continuing to permit axial movement of the cord 30 through the channel 15 of the housing 14.

Figure 8:
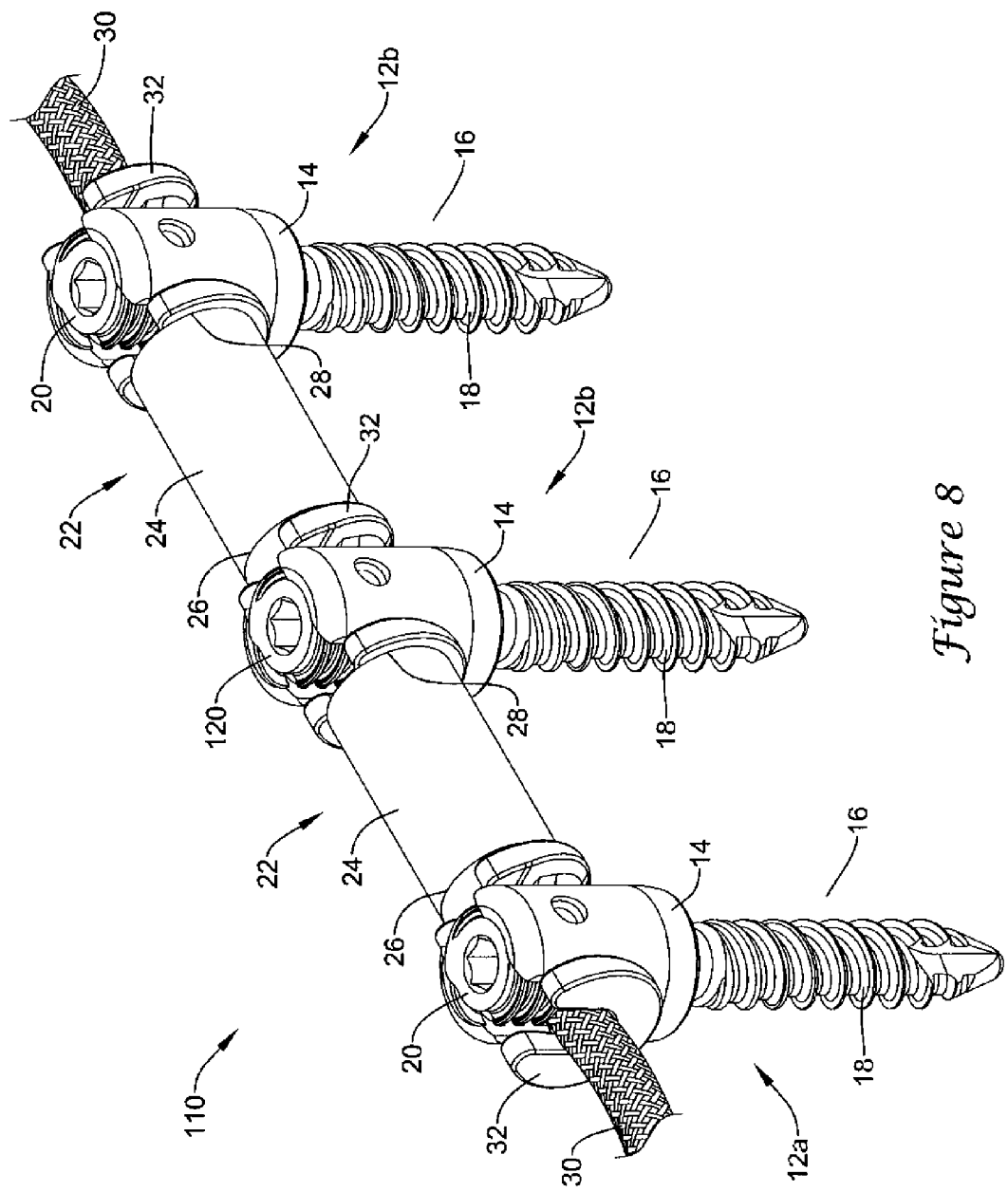
FIG. 8 is a perspective view of another exemplary spinal stabilization system.

FIG. 8 illustrates an exemplary multi-level spinal fixation system 110 for stabilizing a portion of a spinal column utilizing the construct of FIGS. 7A and 7B. The spinal fixation system 110 may include a first pedicle screw 12a configured to be secured to a first vertebra, a second pedicle screw 12b configured to be secured to a second vertebra, and a third pedicle screw 12c configured to be secured to a third vertebra, with the second pedicle screw 12b positioned between the first and third pedicle screws 12a, 12c. The spinal fixation system 110 may include additional pedicle screws 12 configured to be secured to additional vertebrae if desired.

The spinal fixation system 110 may include a support construct 22 positioned between the first and second pedicle screws 12a, 12b and between the second and third pedicle screws 12b, 12c. For instance, a first spacer 24 may be positioned between the first and second pedicle screws 12a, 12b and a second spacer 24 may be positioned between the second and third pedicle screws 12b, 12e. A cord 30 may extend through a bore of each of the spacers 24 and through the channel 15 of the housing 14 of each of the first, second and third pedicle screws 12a, 12b, 12c.

It is noted that during a medical procedure the portions of the cord 30 which are shown extending from the housings 14 of the pedicle screws 12a, 12c may be trimmed as desired to reduce and/or eliminate the portion of the cord 30 extending from the pedicle screws 12a, 12c.

When implanted in a patient, the cord 30 of the spinal stabilization system 10 may limit the range of flexion of the spinal segment, whereas the spacers 24 may limit the range of extension of the spinal segment. For instance, the cord 30 may be placed in tension and the spacers 24 may be placed in compression between the pedicle screws 12a, 12b, 12c.

The spinal stabilization system 10 may also include inserts 32 with a medial portion 38 positionable in the channels 15 of the pedicle screws 12 and first and second flanges 34, 36 located on opposing sides of the housing 14 of a pedicle screw 12. So arranged, end surfaces 48 of the inserts 32 may be configured to abut an end surface of a spacer 24, as described above. The insert 32 may be positioned in the channel 15 in a top-loaded fashion in which the insert 32 is moved into the channel 15 of the housing 14 in a direction generally perpendicular to the longitudinal axis of the channel 15 of the housing 14.

The open channel 40 of each of the inserts 32 may be configured to receive the cord 30 therein. For instance, the open channel 40 of the inserts 32 allows the cord 30 to be inserted into the open channel 40 of the inserts 32 in a direction generally perpendicular to the longitudinal axis of the open channel 40. The slots 39 in the first and second flanges 34, 36 of the inserts 32 allow the cord 30 to be inserted into the open channel 40 while extending outward from the first and second flanges 34, 36.

As shown in FIG. 8, fasteners 20 may be rotatably engaged with the housings 14 of the first and third pedicle screws 12a, 12c to lock the housings 14 of the first and third pedicle screws 12a, 12c from pivotal movement while clamping the cord 30 in the housings 14 of the poly-axial pedicle screws 12a, 12c through direct contact of the fastener 20 against the cord 30, as discussed above. However, it may be desirable to lock the housing 14 of the second or intermediate pedicle screw 12b while allowing the cord 30 to freely move in an axial direction relative to the housing 14 of the second pedicle screw 12b. In such an instance, the fastener 120, discussed above referring to FIGS. 7A and 7B, may be rotatably engaged with the housing 14 of the second pedicle screw 12b to achieve this result. As described above, rotation of the upper component 130 of the fastener 120 locks the housing 14 from pivotal movement relative to the shaft 16 of the pedicle screw 12b while continuing to permit axial movement of the cord 30 through the channel 15 of the housing 14.

In other embodiments, it may be desirable to have the cord 30 clamped in the housing 14 of the second pedicle screw 12b. In such an instance, a fastener 20 may be chosen to lock the housing 14 of the second pedicle screw 12b from pivotal movement while clamping the cord 30 in the housing 14 of the poly-axial pedicle screw 12b through direct contact of the fastener 20 against the cord 30, as discussed above.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A spinal stabilization system comprising:
    a polyaxial pedicle screw including a housing and a threaded shaft extending from the housing, the threaded shaft pivotable relative to the housing to a plurality of angular positions, the housing including a channel extending from a first side of the housing to a second side of the housing;
    an insert positionable in the channel of the housing, the insert including an open channel extending from a first end surface of the insert to a second end surface of the insert, wherein the open channel is defined as a recessed area between a first edge of the insert and a second edge of the insert and opening to a periphery of the insert;
    a support construct including a spacer and a cord extendable through a lumen of the spacer, the cord positionable in the open channel of the insert such that a first portion of the cord extends from the first side of the housing of the polyaxial pedicle screw and a second portion of the cord extends from the second side of the housing of the polyaxial pedicle screw; and
    a fastener configured to rotatably engage the housing of the polyaxial pedicle screw, wherein rotational engagement of the fastener with the housing causes the fastener to directly contact the cord to exert a clamping force directly on the cord, and to directly contact the first and second edges of the insert only once the cord has been compressed between the fastener and the insert a predetermined amount;
    wherein further rotational engagement of the fastener with the housing does not increase compression of the cord between the fastener and the insert beyond the predetermined amount;
    wherein the insert includes a first flange proximate the first end of the insert, a second flange proximate the second end of the insert, and a medial portion extending between the first flange and the second flange, the first flange positionable exterior of the housing and facing the first side of the housing and the second flange positionable exterior of the housing and facing the second side of the housing; and
    wherein the first flange includes a slot extending from the open channel to a peripheral edge of the first flange and the second flange includes a slot extending from the open channel to a peripheral edge of the second flange, such that the cord can be positioned in the open channel through movement of the cord in a direction perpendicular to a longitudinal axis of the open channel.

2. The spinal stabilization system of claim 1, wherein rotational engagement of the fastener with the housing exerts a locking force against a head of the threaded shaft to lock the housing from pivotal movement relative to the threaded shaft.

3. The spinal stabilization system of claim 1, wherein the insert is configured such that when the fastener directly contacts the first and second edges of the insert, the fastener is prevented from further compressing the cord.

4. The spinal stabilization system of claim 1, wherein the open channel of the insert includes a concave surface extending between a first upper edge of the open channel and a second upper edge of the open channel.

5. A spinal stabilization system comprising:
    a polyaxial pedicle screw including a housing pivotably coupled to a threaded shaft, the housing including a channel extending from a first side of the housing to a second side of the housing;
    a spool including a first flange, a second flange, a medial portion extending between the first flange and the second flange, and an open channel extending from a first end surface of the spool to a second end surface of the spool, the spool being configured to engage the housing of the pedicle screw such that the medial portion is positioned in the channel with the first flange positioned adjacent the first side of the housing and the second flange positioned adjacent the second side of the housing;

a spacer having a first end, a second end and a lumen extending through the spacer from the first end to the second end, the first end of the spacer positionable in abutting contact with the first flange of the spool;

a flexible cord configured to extend through the lumen of the spacer and through the spool such that a first portion of the flexible cord extends from the first flange of the spool and a second portion of the flexible cord extends from the second flange of the spool; and a monolithic fastener configured to rotatably engage the housing of the pedicle screw to directly contact and press against the cord such that the cord is compressed between the fastener and a surface of the spool, wherein the fastener directly contacts and exerts a clamping force directly on the medial portion of the spool to lock the housing from pivotal movement relative to the threaded shaft, and wherein the fastener only directly contacts the medial portion of the spool once the cord has been compressed between the fastener and the spool a predetermined amount; and wherein the first flange includes a slot extending from the open channel to a peripheral edge of the first flange and the second flange includes a slot extending from the open channel to a peripheral edge of the second flange, such that the flexible cord can be positioned in the open channel through movement of the cord in a direction perpendicular to a longitudinal axis of the open channel.

6. The spinal stabilization system of claim 5, wherein a force exerted on the cord by the fastener is transferred through the spool to lock the housing from pivotal movement relative to the threaded shaft of the polyaxial pedicle screw.

7. The spinal stabilization system of claim 5, wherein the medial portion includes a first upper edge on a first side of the open channel and a second upper edge on a second side of the open channel opposite the first side, the open channel dimensioned such that the fastener directly contacts the first and second upper edges of the medial portion once the cord is compressed the predetermined amount between the fastener and the spool.

8. A method of stabilizing a spinal segment, comprising:
securing a polyaxial pedicle screw to a vertebra, the polyaxial pedicle screw including a housing pivotably coupled to a threaded shaft, the housing including a channel extending from a first side of the housing to a second side of the housing;

inserting an insert into the channel of the housing of the polyaxial pedicle screw, the insert including an open channel open to a periphery of the insert and extending from a first end surface of the insert to a second end surface of the insert, a first flange proximate the first end of the insert, a second flange proximate the second end of the insert, and a medial portion extending between the first flange and the second flange, the first flange positionable exterior of the housing and facing the first side of the housing and the second flange positionable exterior of the housing and facing the second side of the housing and wherein the first flange includes a slot extending from the open channel to a peripheral edge of the first flange and the second flange includes a slot extending from the open channel to a peripheral edge of the second flange;

positioning a flexible cord in the open channel of the insert such that a first portion of the flexible cord extends from the first end of the insert and a second portion of the flexible cord extends from the second end of the insert;

rotatably engaging a fastener having a lower portion with the housing a first rotational amount such that the lower portion of the fastener rotates into and directly presses against the cord to exert a compressive force on the cord; and further rotatably engaging the fastener with the housing a second rotational amount such that the fastener only directly contacts the insert once the flexible cord has been compressed between the fastener and the insert a predetermined amount;

wherein further rotation of the fastener beyond the second rotational amount does not increase the compressive force exerted on the cord beyond the predetermined amount.

9. The method of claim 8, wherein direct contact between the fastener and the insert exerts a clamping force directly on a head portion of the threaded shaft of the polyaxial pedicle screw to lock the housing from pivotal movement relative to the threaded shaft.

10. The method of claim 8, wherein the open channel of the insert has a longitudinal axis parallel to a central longitudinal axis of the flexible cord, wherein the flexible cord is positioned in the open channel of the insert by moving the flexible cord in a direction generally perpendicular to the longitudinal axis of the open channel and the central longitudinal axis of the flexible cord.

* * * * *